United States Patent
Ein-Gal

(10) Patent No.: US 9,381,380 B2
(45) Date of Patent: Jul. 5, 2016

(54) LOW INTENSITY SHOCKWAVE TREATMENT

(71) Applicant: Moshe Ein-Gal, Ramat Hasharon (IL)

(72) Inventor: Moshe Ein-Gal, Ramat Hasharon (IL)

( * ) Notice: Subject to any disclaimer, the term of this patent is extended or adjusted under 35 U.S.C. 154(b) by 291 days.

(21) Appl. No.: 14/020,856

(22) Filed: Sep. 8, 2013

(65) Prior Publication Data

US 2015/0073312 A1    Mar. 12, 2015

(51) Int. Cl.
*A61N 7/00* (2006.01)
*A61B 17/225* (2006.01)

(52) U.S. Cl.
CPC ............... *A61N 7/00* (2013.01); *A61B 17/2251* (2013.01); *A61B 17/2255* (2013.01); *A61N 2007/0065* (2013.01)

(58) Field of Classification Search
CPC ....................... A61B 17/22012; A61B 17/2251; A61B 17/2255; A61B 2017/22015; A61B 2017/22025; A61N 2007/0065; A61N 1/36107
See application file for complete search history.

(56) References Cited

U.S. PATENT DOCUMENTS

| 5,178,135 A | * | 1/1993 | Uchiyama | A61B 17/2255 600/439 |
| 5,515,415 A | * | 5/1996 | Herrmann | A61B 17/2255 378/195 |
| 5,931,783 A | * | 8/1999 | Redano | A61B 5/4393 600/439 |
| 2007/0239074 A1 | * | 10/2007 | Ein-Gal | A61B 17/2251 601/2 |

OTHER PUBLICATIONS

"Penile Shockwave Therapy Helps Men With Severe Erectile Dysfunction", Medscape, Mar. 22, 2011, found at http://www.medscape.com/viewarticle/739414.

* cited by examiner

*Primary Examiner* — Bo J Peng
(74) *Attorney, Agent, or Firm* — Dekel Patent Ltd.; David Klein

(57) ABSTRACT

A low intensity shockwaves (LISW) system includes a support surface for a patient to sit upon, a shockwave generating device including focusing apparatus operative to focus shockwaves generated by the shockwave generating device to a target, and an organ interface member on the support surface operative to direct the shockwaves to a peritoneum or penile shaft of the patient when the patient sits upon the support surface.

9 Claims, 2 Drawing Sheets

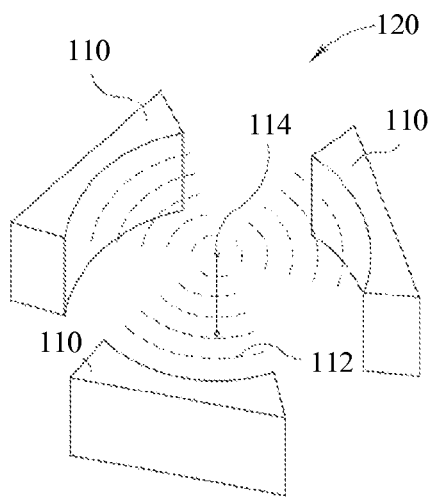
FIG. 2A
PRIOR ART
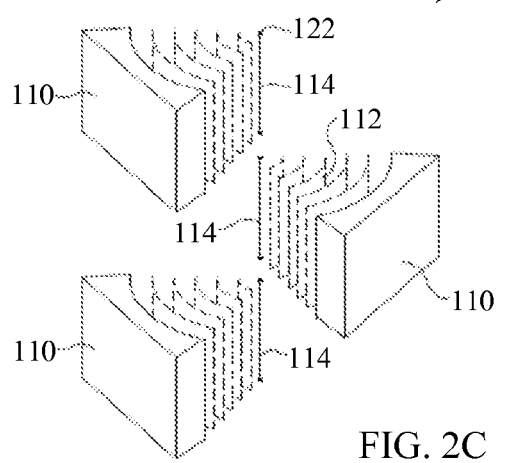
FIG. 2C
PRIOR ART
FIG. 2B
PRIOR ART

LOW INTENSITY SHOCKWAVE TREATMENT

FIELD OF THE INVENTION

The present invention generally relates to a method and device for producing extracorporeal shockwaves, particular in the area of the pelvis, peritoneum or penis, such as for the treatment of erectile dysfunction.

BACKGROUND OF THE INVENTION

Low Intensity Shockwaves (LISW) applied to soft tissue is known to increase blood flow in the tissue. LISW has been used to treat erectile dysfunction (ED), by increasing blood flow to the corpus cavernosum. Normal erectile function requires adequate penile arterial inflow, sufficient corpora cavernosal expansion, and competent venous sinusoidal outflow occlusion. By permitting blood to flow into but not out of the corpus cavernosum, the venous sinusoidal mechanism can transform the corpus cavernosum from an open to a closed chamber capable of trapping blood and thus producing rigid erections.

Prof. Yoram Vardi, head of the neuro-urology unit at Rambam Medical Center in Haifa, Israel, has demonstrated the efficacy of LISW to treat ED (see, for example, "Penile Shockwave Therapy Helps Men With Severe Erectile Dysfunction", Medscape, Mar. 22, 2011, which may be found at http://www.medscape.com/viewarticle/739414). The patient is in a supine position on a treatment table. The operator manually presses a transducer head laterally against the penile shaft while the shaft is firmly held by the operator's other hand. Shockwaves, geometrically focused to a focal point, are applied at several locations along the shaft and at the lower abdomen for treating the crus penis (the part of the corpus cavernosum inside the body). For example, during each treatment session, low-energy shockwave therapy is applied to the penile shaft and crus for 3 minutes in 5 different penile anatomical sites. The shockwaves are generally one tenth the level of intensity as shockwaves used to pulverize kidney stones.

Shockwave devices typically generate shockwaves that converge on a single focal point. Consequently a focal therapeutic volume in the shape of an ellipsoid is created where the long ellipsoid axis coincides with the beam propagation direction and the width of the therapeutic volume is in the order of few mm. This has been adequate in the treatment of stones or orthopedic conditions. However, for treating ED there are major drawbacks: the target is the two corpora cavernosa—shaped like elongated cylinders, located partially in the penis and continuing inside the body as to form the penis crura. A shockwave transducer incorporating a therapeutic focal point must be moved to multiple positions along the penis. Attaching such a transducer head to the lower abdomen so as to apply shockwaves to the crura is geometrically inefficient since the crura are positioned at the lower part of the pelvis, somewhat parallel to the perineum.

A subsequent development (the RENOVA system, manufactured by Initia Ltd. of Israel) treats the crus by coupling a transducer head to the perineum of a patient in a lithotomy position. To effectively optimize shockwave application to the penis and crura anatomy, RENOVA uses linear shockwave therapy (LSWT) incorporating means to focus shockwaves along a linear segment. LSWT enables generation of a 70 mm long treatment volume along the target organ as opposed to the traditional focal point generated by all other shockwave devices.

In all of the known prior art, the patient is lying on his back, the penis is positioned vertically, the shockwaves propagate horizontally and attachment pressure is applied by pressing the transducer against the patient. The attachment pressure, i.e., the pressure applied by the flexible membrane of the transducer head when pressed against the patient, is an important parameter affecting the efficacy of the shockwaves transmission to the patient. Typically, the higher the attachment pressure—the higher the fraction of the shockwaves propagating into the patient. A thin layer of air or air bubbles between the transducer head and the patient may block the propagation.

Consequently, prior art devices rely on an operator—a physician or a technician—to provide the required attachment pressure.

For the purpose of this invention, low intensity shockwaves are pulsed acoustic waves whose wave front is not necessarily steep as is characteristic of high intensity shockwaves.

SUMMARY OF THE INVENTION

The present invention seeks to provide novel methods and apparatus for producing and coupling extracorporeal shockwaves, particular in the area of the pelvis, peritoneum or penis, such as for the treatment of erectile dysfunction, as is described more in detail hereinbelow. The invention produces low-intensity shockwaves so as to significantly improve penile hemodynamics required for erection.

The invention describes a method and device for coupling shockwaves to the perineum and/or to the penile shaft of a patient wherein the patient is seated on a treatment support surface. The transducer (incorporated in the support surface) is positioned so as to direct shockwaves propagation generally upwards. The membrane enclosing the transducer head—which includes propagation liquid (shockwave transmission liquid)—is configured to protrude out of the seat so as to allow coupling the transducer head to the perineum or to the penile shaft. It is advantageous to focus the shockwaves along a line segment. Sufficient pressure of the propagating liquid in the transducer head combined with the patient's weight provide the necessary attachment pressure between the perineum and the transducer head membrane so as to treat the crura. Pressing the penis down toward the transducer head membrane by the patient may provide attachment pressure required for treating the penis. An operator, therefore, is not required for applying the attachment pressure, opening the door for the possibility of performing the treatment at home.

BRIEF DESCRIPTION OF THE DRAWINGS

The present invention will be understood and appreciated more fully from the following detailed description, taken in conjunction with the drawings in which:

FIG. 2A is a simplified pictorial illustration of a multiplicity of discrete source-elements of the prior art, useful with an embodiment of the invention;

FIG. 2B is a simplified pictorial illustration of a prior art linear array of discrete source-elements arranged to form a continuous surface, useful with an embodiment of the invention; and FIG. 2C is a simplified pictorial illustration of an arrangement of prior art discrete source-elements, useful with an embodiment of the invention.

DETAILED DESCRIPTION OF EMBODIMENTS

Figure 1A:
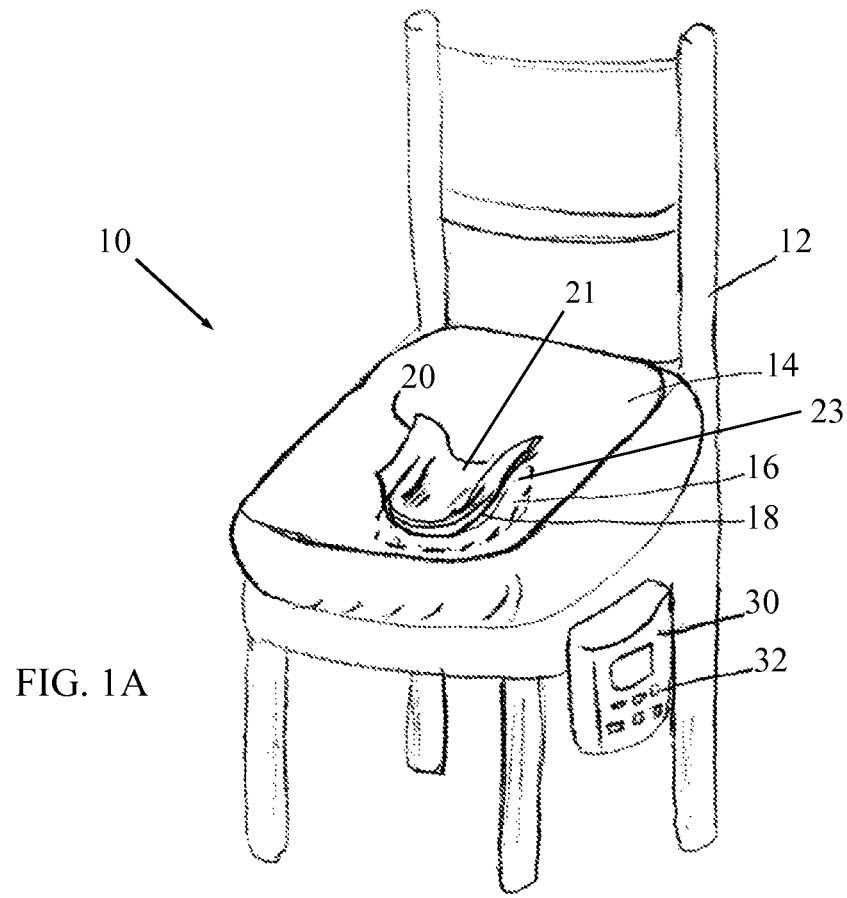
FIGS. 1A and 1B are simplified illustrations of a LISW system, respectively without and with a patient, constructed and operative in accordance with an embodiment of the present invention, with a shockwave transducer incorporated in a support surface for emitting shockwaves to the area of the peritoneum or penile shaft while the patient is in a sitting position.

Reference is now made to FIG. 1A, which illustrates a LISW system 10, such as for treating ED, in accordance with a non-limiting embodiment of the present invention.

The system 10 includes a support surface 14 for a patient to sit upon. In the illustrated embodiment, the support surface 14 is part of a chair 12 with legs that rest on a floor. In other embodiments, the support surface 14 may be a seat similar to a bicycle seat or motorcycle seat, wherein the patient sits in a slightly crouching position. Such an arrangement may provide better shockwaves coupling to the crura and the penis.

A shockwave generating device 16 is provided for generating shockwaves. As is well known in the art, in one type of shockwave generating device (the invention can be carried out with other types of shockwave generators, too), the device converts electrical energy into acoustic waves, such as by generating a strong pulse of an electric or magnetic field, usually by capacitor discharge, converting the electromagnetic field into acoustic energy, and directing the energy to a small target by means of an associated focusing apparatus 18. Some of the types of geometry used in acoustic wave generation and focusing include, without limitation, point source and ellipsoidal reflector, planar source and acoustic lens, cylindrical source and parabolic reflector, and spherical source with no additional focusing, and a truncated conical source with parabolic reflector.

In accordance with an embodiment of the present invention, the focusing apparatus 18 is operative to focus the shockwaves onto a line segment, such as but not limited to, in any of the shockwave devices of US Patent Application 20070239074 to Ein-Gal, the contents of which are incorporated herein by reference. Examples of such shockwave generating devices with focusing apparatus are explained below with reference to FIGS. 2A-2C.

Figure 1B:
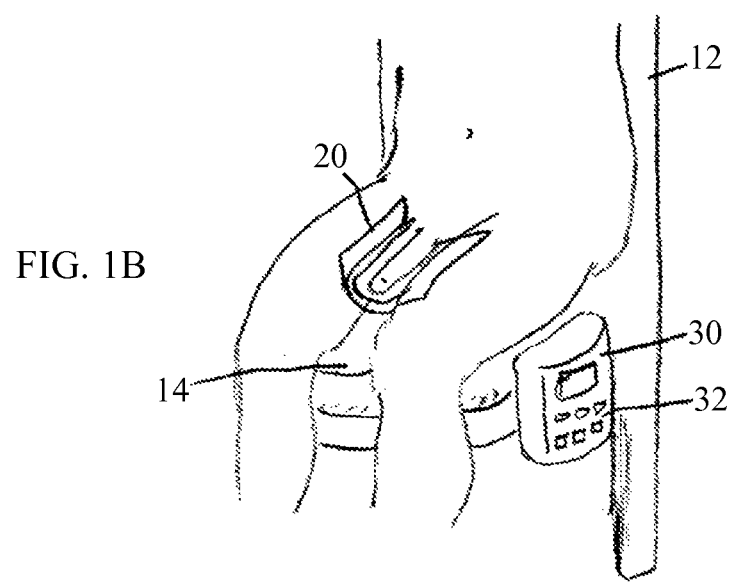

Referring to FIGS. 1A and 1B, an organ interface member 20 (also referred to as a transducer head 20) on the support surface 14 directs the shockwaves from the shockwave generating device 16 to a peritoneum or penile shaft (or both) of the patient when the patient sits upon the support surface 14. Although the organ interface member 20 may be flush with support surface 14, in a preferred embodiment, a portion of the organ interface member 20 protrudes out of support surface 14, such as a membrane 21 arranged to contact the peritoneum or penile shaft or both. A shockwave transmission liquid 23 (e.g., water) may be sealed inside organ interface member 20 by membrane 21. The organ interface member 20 is curved to at least partially cover the peritoneum or penile shaft or both.

The shockwave generating device 16 and focusing apparatus 18 are shown in broken lines hidden underneath the support surface 14, but may alternatively be flush or above this surface (such as to the side of the organ interface member 20).

A controller 30 with a user interface 32 may be provided to control the operation of the shockwave generating device 16. Such a controller may be, without limitation, very similar to the controlling equipment of the RENOVA system, manufactured by Initia Ltd. of Israel. The organ interface member 20 is positioned so as to direct the shockwaves generally upwards with respect to the support surface 14.

Accordingly, the system 10 is used to apply shockwaves to the peritoneum or penile shaft of the patient while sitting on the support surface 14. The patient himself may apply pressure on the organ interface member 20 to modify the manner in which the shockwaves improve the penile blood flow so as to treat erectile dysfunction of the patient.

Examples of shockwave generating devices with focusing apparatus are explained now with reference to FIGS. 2A-2C. For example, a plurality of point sources may be arranged along a line, each point source cooperating with an ellipsoidal reflector to focus the energy at the other focus of the ellipsoidal reflector. Since the point sources are arranged along a line, the resultant energy is focused on a line-focus segment. Another example is a line source (e.g., a piezoelectric line source) which generates waves along a line that are focused with an acoustic lens. The same line source may be focused with a parabolic reflector to a line focus. Yet another example is a plurality of directional point sources arranged along a line that emit waves to a line focus.

Reference is now made to FIG. 2A. In this example, there is a coplanar arrangement 120 of discrete source-segments 110. Shockwaves 112 generated by the individual source-segments 110 propagate toward line-focus segment 114.

Reference is now made to FIG. 2B. In this example, a linear array 130 of discrete source-elements 110 is arranged to form a continuous surface. Each discrete source-element 110 focuses acoustic waves 112 upon a line-focus segment 114 thus forming finite linear line focus 122.

Reference is now made to FIG. 2C. In this example, a multiplicity of source-elements 110 are distributed on different planes and at different rotational locations around a rotation axis which is coterminous with finite linear line focus 122 composed of discrete line-focus segments 114.

What is claimed is:

1. A low intensity shockwaves (LISW) system comprising:
   a support surface for a patient to sit upon, said support surface comprising a crotch portion positioned to be between legs of the patient sitting on said support surface;
   a shockwave generating device comprising focusing apparatus operative to focus shockwaves generated by said shockwave generating device to a target; and
   an organ interface member comprising an elongate membrane having a longitudinal length and a base and curved sides that extend upwards from said base along the longitudinal length forming a U-shaped receiving portion, said elongate membrane being located on said crotch portion of said support surface, wherein said organ interface member is operative to couple the shockwaves from said shockwave generating device to a peritoneum or penile shaft of the patient when the patient sits upon said support surface.

2. The system according to claim 1, wherein said shockwave generating device comprises a shockwave transmission liquid, wherein said membrane is operable to transmit shockwaves produced by the shockwaves generating device and propagating in the shockwave transmission liquid.

3. The system according to claim 1, wherein said organ interface member is elongated so as to couple shockwaves to the target along a line segment.

4. The system according to claim 1, wherein said organ interface member is positioned so as to direct the shockwaves generally upwards with respect to said support surface.

5. The system according to claim 1, wherein a portion of said organ interface member protrudes out of said support surface.

6. The system according to claim 1, wherein said focusing apparatus is operative to focus the shockwaves onto a line segment.

7. A method comprising using the system of claim 1, comprising a patient sitting on said support surface and placing a peritoneum or penile shaft of the patient on to said elongate membrane so that the peritoneum or penile shaft lies in the U-shaped receiving member and the curved sides touch the peritoneum or penile shaft, and applying shockwaves that are transferred by said membrane to the peritoneum or penile shaft.

8. The method according to claim 7, further comprising applying pressure on said organ interface member.

9. The method according to claim 7, further comprising applying the shockwaves to treat erectile dysfunction of the patient.

* * * * *